(12) United States Patent
Suenaga et al.

(10) Patent No.: US 12,066,384 B2
(45) Date of Patent: Aug. 20, 2024

(54) QUALITY CONTROL METHOD FOR DIISONONYL PHTHALATE, PRODUCING METHOD FOR RESIN COMPOSITION, RESIN COMPOSITION, AND CABLE OR TUBE

(71) Applicant: Hitachi Metals, Ltd., Tokyo (JP)

(72) Inventors: Kazufumi Suenaga, Tokyo (JP); Ryutaro Kikuchi, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 842 days.

(21) Appl. No.: 17/152,462

(22) Filed: Jan. 19, 2021

(65) Prior Publication Data

US 2021/0231569 A1  Jul. 29, 2021

(30) Foreign Application Priority Data

Jan. 24, 2020  (JP) .................. 2020-010429

(51) Int. Cl.
| | |
|---|---|
| *G01N 21/65* | (2006.01) |
| *C07C 69/80* | (2006.01) |
| *C08K 5/12* | (2006.01) |
| *C08L 27/06* | (2006.01) |

(52) U.S. Cl.
CPC ............ *G01N 21/65* (2013.01); *C07C 69/80* (2013.01); *C08K 5/12* (2013.01); *C08L 27/06* (2013.01); *C08L 2203/206* (2013.01)

(58) Field of Classification Search
CPC ...................................... G01N 21/65
See application file for complete search history.

(56) References Cited

U.S. PATENT DOCUMENTS

2017/0138850 A1* 5/2017 Noguchi ............... G01N 21/35

FOREIGN PATENT DOCUMENTS

| EP | 3 187 857 A1 | 7/2017 |
|---|---|---|
| WO | WO 2016/031063 A1 | 3/2016 |

* cited by examiner

*Primary Examiner* — Michael F Pepitone
(74) *Attorney, Agent, or Firm* — MCGINN I.P. LAW GROUP, PLLC.

(57) ABSTRACT

A quality control method for a diisononyl phthalate includes a measuring step of irradiating the diisononyl phthalate with a laser to measure a Raman spectrum; and an acceptance or rejection decision step of determining an acceptance or a rejection of a quality of the diisononyl phthalate on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum.

15 Claims, 14 Drawing Sheets

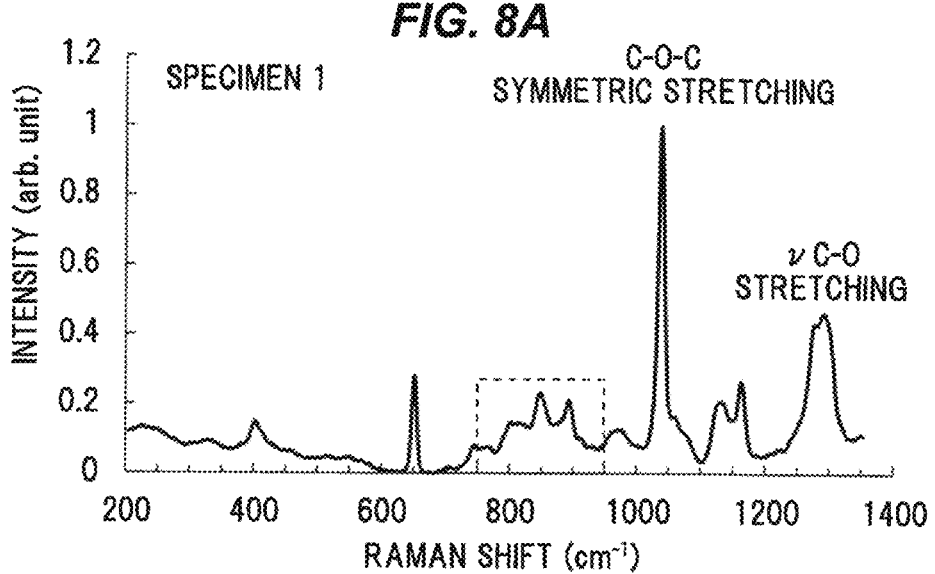
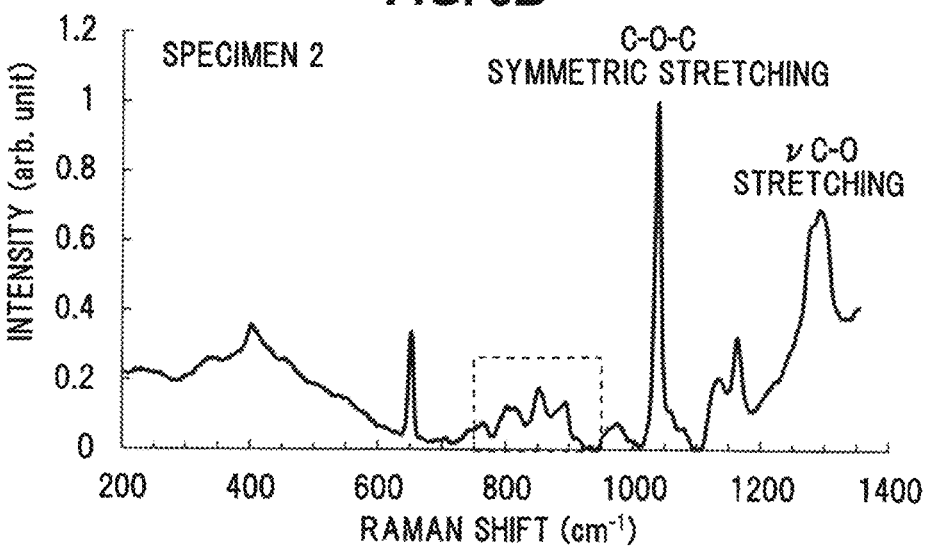
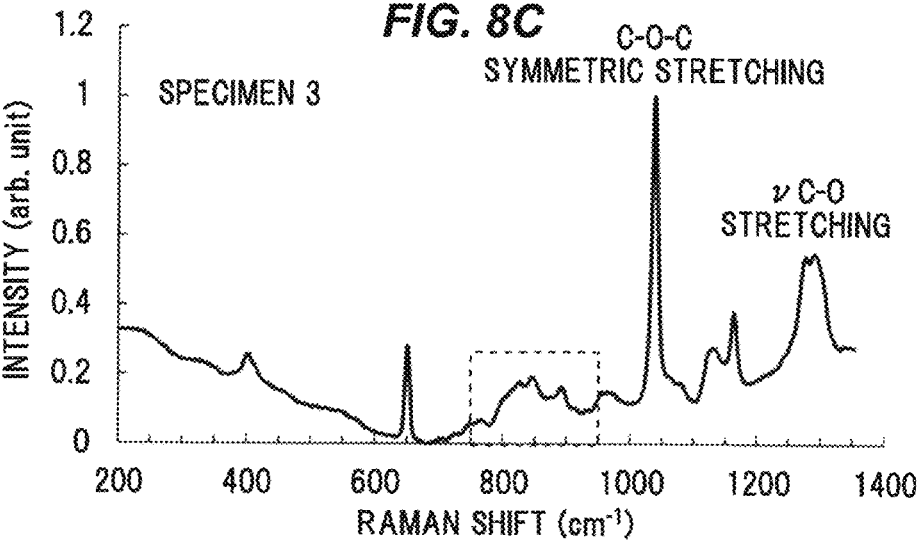

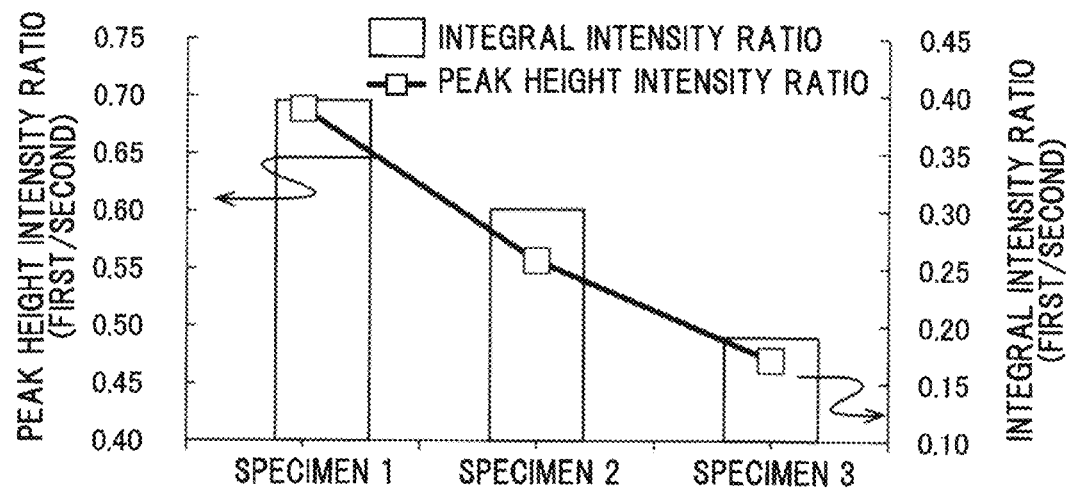
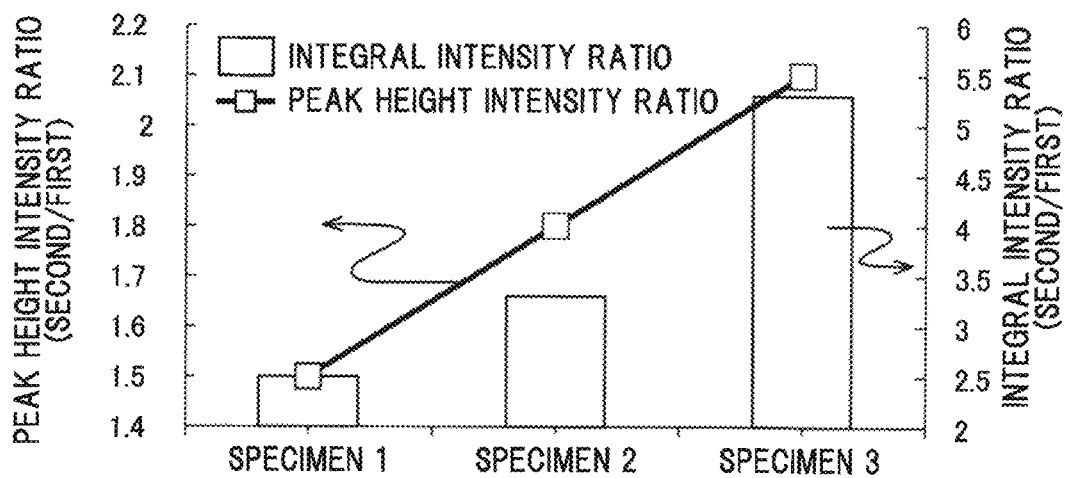

US 12,066,384 B2

QUALITY CONTROL METHOD FOR DIISONONYL PHTHALATE, PRODUCING METHOD FOR RESIN COMPOSITION, RESIN COMPOSITION, AND CABLE OR TUBE

CROSS-REFERENCE TO RELATED APPLICATION

The present application is based on Japanese patent application No. 2020-010429 filed on Jan. 24, 2020, the entire contents of which are incorporated herein by reference.

BACKGROUND OF THE INVENTION

1. Field of the Invention

The present invention relates to a quality control method for a diisononyl phthalate, a producing method for a resin composition, a resin composition, and a cable or a tube.

2. Description of the Related Art

Conventionally, as a method for plasticizing a rigid vinyl chloride resin, a method of adding a phthalic acid ester based plasticizer such as a diethylhexyl phthalate (DEHP) or a diisononyl phthalate (DINP) or the like has been known (see, e.g., WO 2016/031063).

On the other hand, recently, from the point of view of environmental friendliness, the movement to replace the DEHP, which has been widely used so far, with the DINP has been activated.

[Patent Document 1] WO 2016/031063

SUMMARY OF THE INVENTION

An alcohol that is a raw material for the DEHP is a 2-ethylhexanol that is produced through the production of a naphtha, a propylene, and a normal butyraldehyde. For this reason, even when the DEHP produced by a different producer is used, the variation in the performance of the vinyl chloride resin mixture, which is a vinyl chloride resin to which the DEHP has been added, is small.

However, an isononyl alcohol, which is a raw material alcohol for the DINP, is produced by a complicated process through the production of a naphtha, a B-B fraction (C4), a RAF (raffinate) 1, a RAF 2, a n-butene, and an octene, and an isomer is liable to be produced. For that reason, when the DINP produced by the different producer is used, a variation in a property such as an embrittlement property and the like is liable to occur.

It is an object of the present invention to provide a quality control method for a diisononyl phthalate (DINP), which is designed to be able to select a DINP that is able to make higher a property such as an embrittlement property and the like when added as a plasticizer for a vinyl chloride resin, a resin composition including a vinyl chloride resin to which the DINP has been added, and which is designed to be excellent in the property such as the embrittlement property and the like, a producing method for the same resin composition, or a cable or a tube including an electrical insulating member made of the same resin composition therein.

For the purpose of solving the above described problems, the present invention provides a quality control method for a diisononyl phthalate, comprising: a measuring step of irradiating the diisononyl phthalate with a laser to measure a Raman spectrum; and an acceptance or rejection decision step of determining an acceptance or a rejection of a quality of the diisononyl phthalate on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum.

(Points of the Invention)

According to the present invention, it is possible to provide the quality control method for the diisononyl phthalate (DINP), which is configured to be able to select the DINP that is able to make higher the property such as the embrittlement property and the like when added as a plasticizer for a vinyl chloride resin, a resin composition including a vinyl chloride resin to which the DINP has been added, and which is excellent in the property such as the embrittlement property and the like, a producing method for the same resin composition, or a cable or a tube including an electrical insulating member made of the same resin composition therein.

BRIEF DESCRIPTION OF THE DRAWINGS

Next, the embodiment of the present invention will be described in accordance with appended drawings:

FIGS. 8A to 8C show Raman spectra for the frozen specimens 1, 2, and 3, respectively, measured in a wave number range of from 200 to 1350 $cm^{-1}$;

FIG. 12A is a graph showing, for the frozen specimens 1, 2, and 3, respective values of the ratios of the peak height intensities of the respective first spectral peaks to the peak height intensities of the respective second spectral peaks, and respective values of the ratios of the integral intensities of the respective first spectral peaks to the integral intensities of the respective second spectral peaks;

FIG. 12B is a graph showing, for the frozen specimens 1, 2, and 3, respective values of the ratios of the peak height intensities of the respective second spectral peaks to the peak height intensities of the respective first spectral peaks, and respective values of the ratios of the integral intensities of the respective second spectral peaks to the integral intensities of the respective first spectral peaks;

DETAILED DESCRIPTION OF THE PREFERRED EMBODIMENTS

Embodiment (Structure of a Diisononyl Phthalate)

A diisononyl phthalate (DINP) is a type of phthalic acid ester, and can be used in a plasticizer for a resin product such as a polyvinyl chloride or the like. When the DINP is added to the polyvinyl chloride, the DINP is inserted between the molecular chains in the polyvinyl chloride, in which the tight bonding between the molecular chains is suppressed and, as a result, the embrittlement temperature of the polyvinyl chloride is lowered.

Figure 1A:
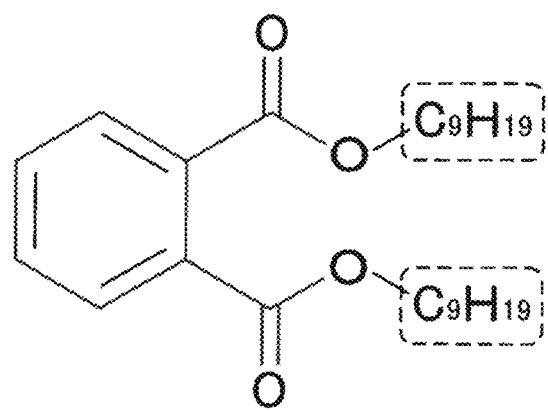
FIGS. 1A to 1C show structural formulas, respectively, for a DINP.
Figure 1B:
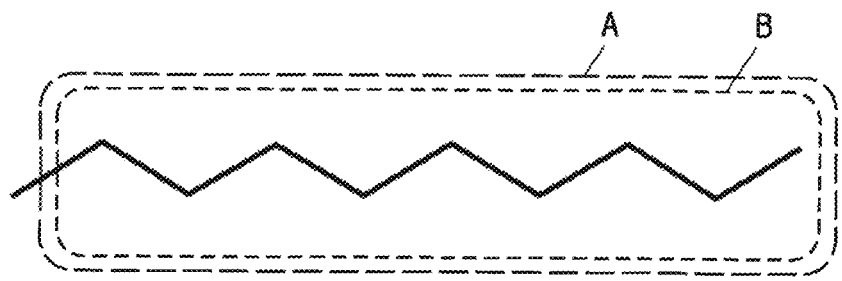
Figure 1C:
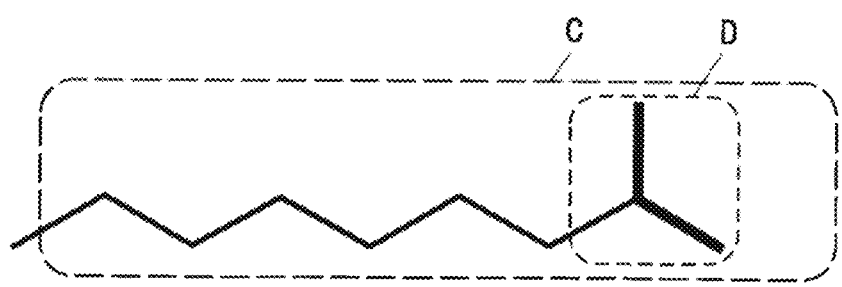

FIGS. 1A to 1C show structural formulas, respectively, for the DINP. It is generally known that the alkyl chain $C_9H_{19}$ of the DINP shown in FIG. 1A has a branched chain type alkyl chain structure (hereinafter referred to as the branched chain type alkyl chain structure), which is derived from a mono methyl octanol, and which has an isopropyl group —$CH(CH_3)_2$ shown in FIG. 1C at a tip thereof (see the above mentioned patent document 1, for example), where the portion surrounded by the broken line C in FIG. 1C denotes the alkyl chain $C_9H_{19}$, while the portion surrounded by the broken line D denotes the isopropyl group —$CH(CH_3)_2$.

The inventors of the present application have found out, by an analysis using the Raman scattering intensity measurement, which will be described later, that the alkyl chain $C_9H_{19}$ of the DINP can, besides having the form of the branched chain type alkyl chain structure, take the form of a straight chain type alkyl chain structure (hereinafter referred to as the straight chain type alkyl chain structure), which has been derived from a n-nonalol, and which has had a molecular chain —$(CH_2)_8$-$CH_3$ in a straight chain hydrocarbon shown in FIG. 1B, and the inventors of the present application have found out that the DINPs produced in a variety of conditions (for example, the DINPs produced by different producers) have varied in the ratios of their respective branched chain type alkyl chain structures and their respective straight chain type alkyl chain structures, in a manner that has caused differences among the performances of the DINPs for the plasticizer. Here, the portion surrounded by the broken line A in FIG. 1B denotes the alkyl chain $C_9H_{19}$, while the portion surrounded by the broken line B in FIG. 1B denotes the molecular chain —$(CH_2)_8$-$CH_3$ in the straight chain hydrocarbon.

Furthermore, the inventors of the present application have found out that the larger the proportion of the straight chain type alkyl chain structures included in the DINP molecules, that is, the larger the value of the ratio of the number of the straight chain type alkyl chain structures to the number of the branched chain type alkyl chain structures in the DINP, the more effectively the embrittlement temperature of the polyvinyl chloride has been lowered. This is considered to be because the DINP molecules having the straight chain type alkyl chain structures composed of the straight chain hydrocarbons have been long as compared to the DINP molecules having the branched chain type alkyl chain structures and, as a result, when the DINP molecules having the straight chain type alkyl chain structures have entered between the molecular chains in the polyvinyl chloride used as a base polymer, it has allowed the molecular chains in the polyvinyl chloride to be spaced farther apart from each other, and has thereby been able to suppress the bonding between the molecular chains in the polyvinyl chloride while keeping the spacing between the molecular chains in the polyvinyl chloride apart even under a low temperature condition.

(Quality Control Method for the Diisononyl Phthalate)

A quality control method for the diisononyl phthalate according to a present embodiment is designed to use the Raman scattering intensity measurement, to be able to select the DINPs which are large in the value of the ratio of the number of the straight chain type alkyl chain structures to the number of the branched chain type alkyl chain structures, from among a plurality of the DINPs produced under a variety of conditions. The Raman scattering intensity measurement enables the non-contact analysis, and thereby is able to maintain the intact DINP information.

The quality control method for the diisononyl phthalate according to the present embodiment is configured to include a measuring step of irradiating the diisononyl phthalate with a laser to measure a Raman spectrum, and an acceptance or rejection decision step of determining an acceptance or a rejection of a quality of the diisononyl phthalate on the basis of a high and low intensity relationship between an intensity (an integral intensity or a peak height intensity) of a first spectral peak, which is ascribed to a vibration of the molecular chains in the straight chain hydrocarbon, and an intensity (an integral intensity or a peak height intensity) of a second spectral peak, which is ascribed to a vibration of the isopropyl groups, in the measured Raman spectrum.

Here, since the molecular chains in the straight chain hydrocarbon constitute the straight chain type alkyl chain structures and the isopropyl groups are included in the straight chain type alkyl chain structures, it is possible to know the large and small number relationship between the number of branched chain type alkyl chain structures and the number of straight chain type alkyl chain structures in the DINP by measuring the above mentioned high and low intensity relationship between the intensity of the first spectral peak, which is ascribed to the vibration of the molecular chains in the straight chain hydrocarbon, and the intensity of the second spectral peak, which is ascribed to the vibration of the isopropyl groups.

The first spectral peak refers to a peak of which the scattering intensity is a maximum within a wave number range of not smaller than 880 cm$^{-1}$ and not larger than 900 cm$^{-1}$ in the Raman spectrum measured under a condition of a measurement temperature of 26 degrees Celsius. Also, the second spectral peak refers to a peak of which the scattering intensity is a maximum within a wave number range of not smaller than 840 cm$^{-1}$ and not larger than 860 cm$^{-1}$ in the Raman spectrum measured under the condition of the measurement temperature of 26 degrees Celsius. Note that the positions of the first spectral peak and the second spectral peak can be shifted within the above ranges of wave numbers, respectively, depending on the temperature and the like of the DINP at the time of the measurement.

Since the first spectral peak and the second spectral peak are measured in a state of being included in a composite waveform in which a plurality of spectral peaks resulting from different molecular vibrations are being combined together, the resolution of the plurality of spectral peaks by the spectral deconvolution is carried out, to determine the respective Raman shifts (cm$^{-1}$) of the first spectral peak and the second spectral peak where the Raman shifts are expressed in wave numbers. For the spectral deconvolution, a statistical distribution function such as the pseudo-Voigt function, the Lorentzian function, the Gaussian distribution function or the like is used.

In the above acceptance or rejection decision step, if, for example, the value of the ratio of the integral intensity of the first spectral peak to the integral intensity of the second spectral peak in the Raman spectrum measured under the condition of the measurement temperature of 26 degrees Celsius is not less than 0.3, then the quality of the DINP to be measured is regarded as accepted. Further, if, for example, the value of the ratio of the peak height intensity of the first spectral peak to the peak height intensity of the second spectral peak in the Raman spectrum measured under the condition of the measurement temperature of 26 degrees Celsius is not less than 0.67, then the quality of the DINP to be measured is regarded as accepted. If the value of the ratio of the integral intensity of the first spectral peak to the integral intensity of the second spectral peak is not less than 0.3, or if the value of the ratio of the peak height intensity of the first spectral peak to the peak height intensity of the second spectral peak is not less than 0.67, then, when the DINP is added to the polyvinyl chloride as the plasticizer, the embrittlement temperature of that polyvinyl chloride can be made sufficiently low.

Here, the peak heights and the integral intensities of the first spectral peak and the second spectral peak are ones computed by using a peak profile obtained by the spectral deconvolution (the fitting analysis) using the aforementioned statistical distribution functions, and they are determined after the background correction of the peak profile being carried out. The background correction of the peak profile is one that is to be carried out in order to eliminate the background influences that are not caused by the molecular structures of the DINP, but that are thought to be caused by inevitable light such as emitted fluorescence, Rayleigh and Mie scattered light, disturbed light other than the irradiated laser light, and the like, and the background correction of the peak profile is carried out by subtracting a background profile (a base line) determined by the fitting analysis using a polynomial function or a spline function or the like from the above mentioned peak profile. Further, the integral ranges in determining the integral intensities of the first spectral peak and the second spectral peak are the ranges between the two points of intersection of the peak profile and the background profile described above.

Note that when it is assumed that all the alkyl chains in the DINP molecules in the DINP take the form of the straight chain type alkyl chain structures, the intensity of the second spectral peak becomes zero and, as a result, in theory, there exists no upper limit on the value of the ratio of the integral intensity of the first spectral peak to the integral intensity of the second spectral peak in the Raman spectrum measured under the condition of the measurement temperature of 26 degrees Celsius. However, in practice, not all of the alkyl chains in the DINP molecules in the DINP take the form of the straight chain type alkyl chain structures and, as a result, the value of the ratio of the integral intensity of the first spectral peak to the integral intensity of the second spectral peak in the Raman spectrum measured under the condition of the measurement temperature of 26 degrees Celsius does not often exceed 1, but in many cases, it is not more than 0.8.

(Resin Composition and Producing Method for the Same)

A resin composition according to the present embodiment is a resin composition composed primarily of the polyvinyl chloride to which the DINP, which has been regarded as accepted by the quality control method for the diisononyl phthalate, has been added. That is, a producing method for the resin composition according to the present embodiment is configured to include a step of adding the DINP regarded as accepted by the quality control method for the diisononyl phthalate to the polyvinyl chloride. Note that, in the step of adding the DINP to the polyvinyl chloride, the DINP in a liquid state (for example, of from 10 degrees Celsius to 35 degrees Celsius) is added to the polyvinyl chloride.

The resin composition according to the present embodiment is configured to include therein, for example, the polyvinyl chloride, and the DINP added to that polyvinyl chloride, with the DINP being configured in such a manner that when the Raman spectrum is measured by irradiating the DINP with the laser under the condition of the measurement temperature of 26 degrees Celsius, the value of the ratio of the integral intensity of the first spectral peak to the integral intensity of the second spectral peak in the measured Raman spectrum is not less than 0.3. Further, an other resin composition according to the present embodiment is configured to include therein, for example, the polyvinyl chloride, and the DINP added to that polyvinyl chloride, with the DINP being configured in such a manner that when the Raman spectrum is measured by irradiating the DINP with the laser under the condition of the measurement temperature of 26 degrees Celsius, the value of the ratio of the peak height intensity of the first spectral peak to the peak height intensity of the second spectral peak in the measured Raman spectrum is not less than 0.67.

The resin composition according to the present embodiment can take a variety of forms in accordance with its intended use. For example, when the above resin composition is used in an electrical insulating member for a cable or a tube, it is worked into a tubular shape, or when the above resin composition is used in an agricultural vinyl, it is worked into a sheet shape.

(Cable or Tube Structure)

The resin composition according to the present embodiment can be used for a material for an electrical insulating member to be used in a cable or a tube. Below are given one example of a configuration of a cable including an electrical insulating member made of the resin composition according to the present embodiment, and one example of a configuration of a tube including an electrical insulating member made of the resin composition according to the present embodiment.

Figure 2A:
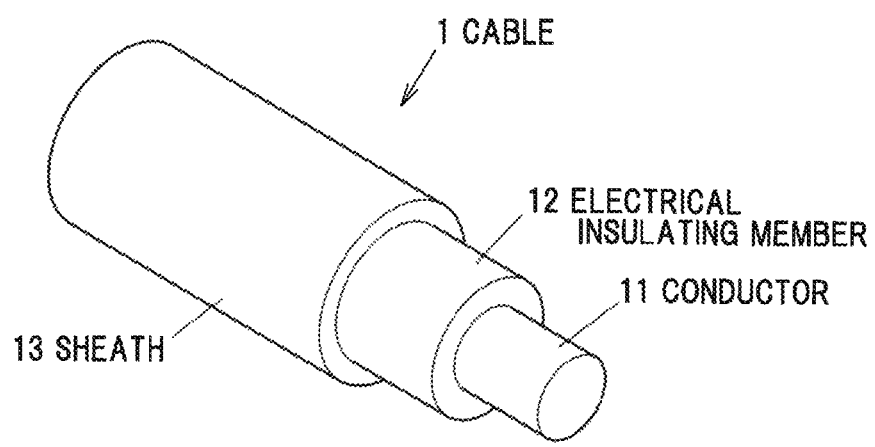
FIG. 2A is a perspective view showing a configuration example of a cable according to a present embodiment.

FIG. 2A is a perspective view showing a configuration example of a cable 1 according to the present embodiment. The cable 1 is being configured in such a manner as to include therein a conductor 11, an electrical insulating member 12, which is being provided over an outer periphery of the conductor 11, and a sheath 13, which is being provided over an outer periphery of the electrical insulating member 12. The conductor 11 is made of a conductor such as a copper or the like, and a stranded wire, which is formed by laying a plurality of lead wires together, may be used as the conductor 11. The electrical insulating member 12 is made of an electrical insulating material such as a foamed polyethylene or the like. The sheath 13 is made of the resin composition according to the present embodiment described above. The cable 1 can be used as, for example, a cable designed for electric wire applications or for medical applications.

Figure 2B:
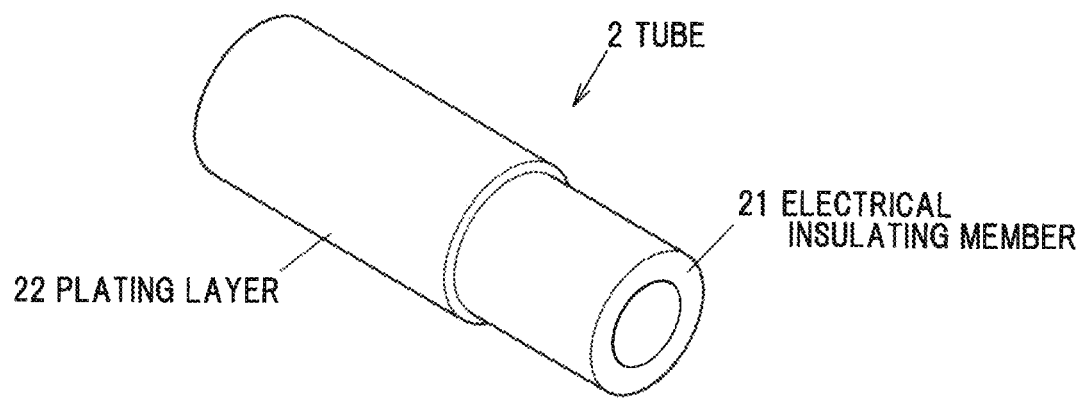
FIG. 2B is a perspective view showing a configuration example of a tube according to the present embodiment.

FIG. 2B is a perspective view showing a configuration example of a tube 2 according to the present embodiment. The tube 2 is being configured in such a manner as to include therein a hollow linear shape electrical insulating member 21, and a plating layer 22, which is being provided over an outer periphery of the electrical insulating member 21. The electrical insulating member 21 is made of the resin composition according to the present embodiment described above. The plating layer 22 is made of a metal such as a copper or the like. The tube 2 can be used for, for example, a waveguide and the like.

Advantageous Effects of the Embodiment

According to the present embodiment, it is possible to provide the quality control method for the diisononyl phthalate, which is able to select the DINP that is able to further enhance the property such as the embrittlement property and the like when used as the plasticizer for the vinyl chloride resin. This quality control method for the diisononyl phthalate allows an estimation of the embrittlement temperature of the vinyl chloride resin with the DINP compounded therein before the DINP is compounded into the vinyl chloride resin, and therefore makes it possible to enhance the production speed and yield of the product such as the vinyl chloride resin with the DINP compounded therein, or the cable using the same vinyl chloride resin, or the tube using the same vinyl chloride resin, or the like.

Further, according to the present embodiment, it is possible to provide the resin composition including the vinyl chloride resin to which the DINP has been added, and which is excellent in the property such as the embrittlement property and the like, and the producing method for the same resin composition. Further, according to the present embodiment, it is possible to provide the cable or the tube including the electrical insulating member made of the resin composition being excellent in the property such as the embrittlement property and the like. In addition, the quality control method for the diisononyl phthalate, and the producing method for the resin composition according to the present embodiment can also be applied to the development of materials using materials informatics (MI) for analyzing data by exploiting machine learning or artificial intelligence (AI) or the like.

EXAMPLES

First, three DINPs (specimens 1, 2, and 3) produced under a variety of conditions were prepared, and the Raman scattering intensity measurement was carried out. The Raman scattering intensity measurement used the RAMAN force Standard VIS-NIR-HS available from Nanophoton Corporation, and was carried out in the following conditions: the laser wavelength was 532 nm, the width of the entrance slit of the spectroscope was 50 µm, the number of ruled grating grooves of the diffraction grating was 1200 gr/mm (the central wave number of the measurement range of wave numbers was 800 $cm^{-1}$), the value of the ratio (attenuation ratio) of the amount of the laser light after attenuation to the maximum amount of the laser light of a Neutral Density (ND) filter was 190/255, and the measurement temperature was 26 degrees Celsius. The specimens 1, 2, and 3 were in a liquid state (the DINPs were liquid at 26 degrees Celsius), and were irradiated with the laser in a state of being put in a container made of aluminum (an aluminum pan).

Figure 3A:
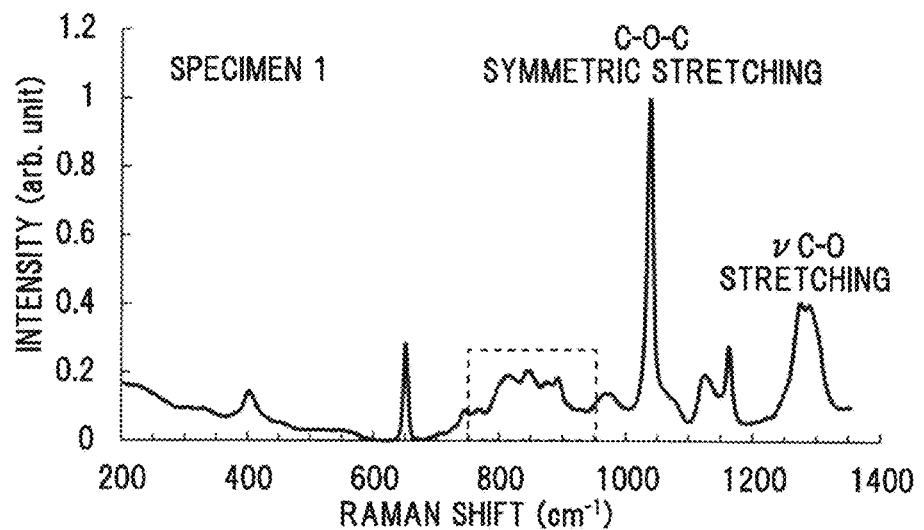
FIGS. 3A to 3C show Raman spectra for specimens 1, 2, and 3, respectively, measured in a wave number range of from 200 to 1350 $cm^{-1}$.
Figure 3B:
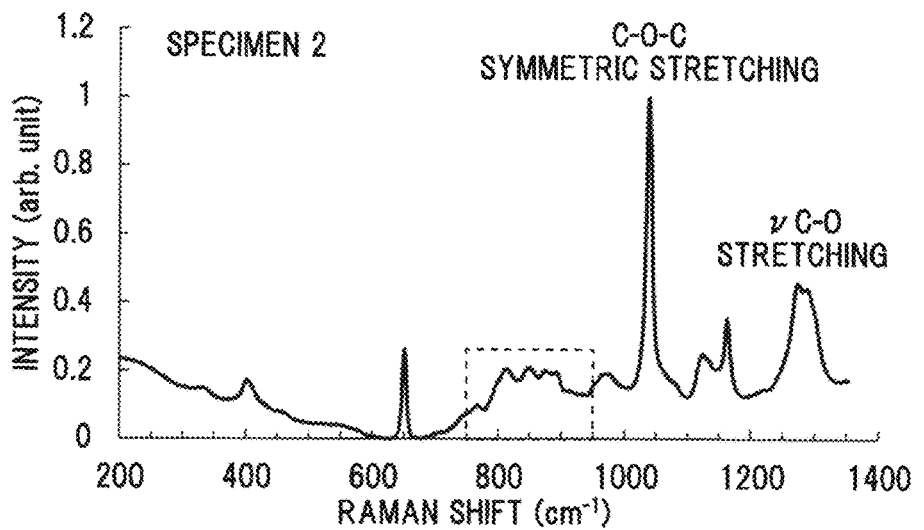
Figure 3C:
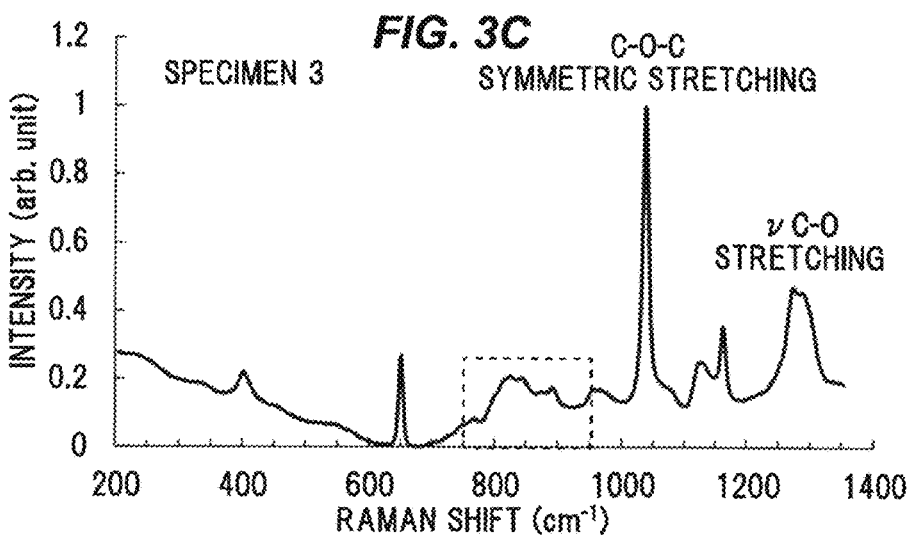

FIGS. 3A to 3C show Raman spectra for the specimens 1, 2, and 3, respectively, measured in a wave number range of from 200 to 1350 $cm^{-1}$. In these Raman spectra of the specimens 1, 2, and 3, the respective spectral peaks at a wave number of approximately 1040 $cm^{-1}$ were the spectral peaks resulting from C—O—C symmetric stretching, while the respective spectral peaks at a wave number of approximately 1280 cm$^{-1}$ were the spectral peaks resulting from vC-O stretching.

Figure 4A:
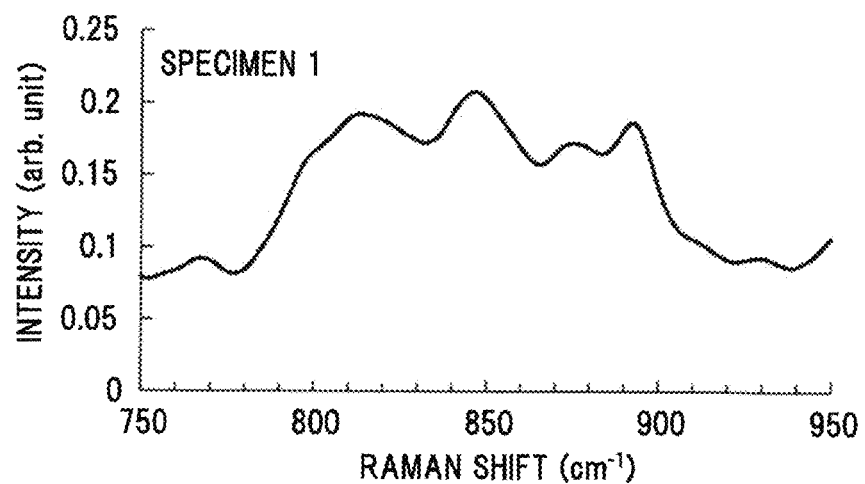
FIG. 4A shows the Raman spectrum for the specimen 1 shown by enlarging a wave number range of from 750 to 950 $cm^{-1}$ in the Raman spectrum for the specimen 1.
Figure 5A:
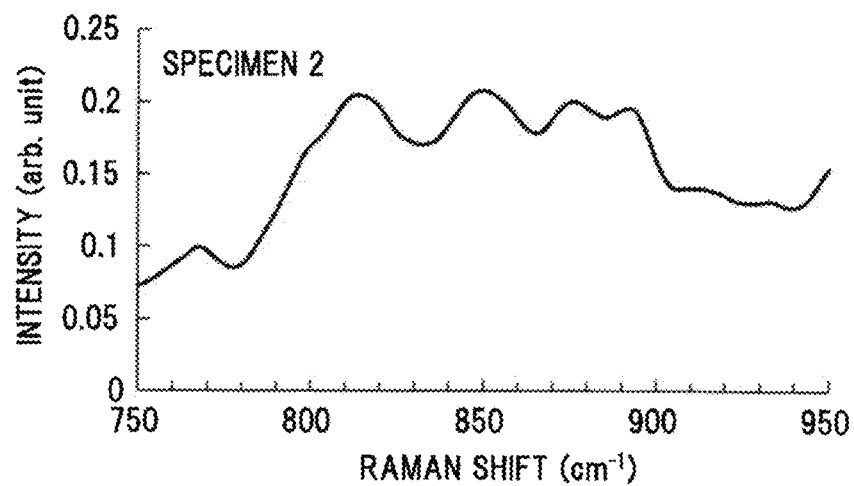
FIG. 5A shows the Raman spectrum for the specimen 2 shown by enlarging a wave number range of from 750 to 950 $cm^{-1}$ in the Raman spectrum for the specimen 2.
Figure 6A:
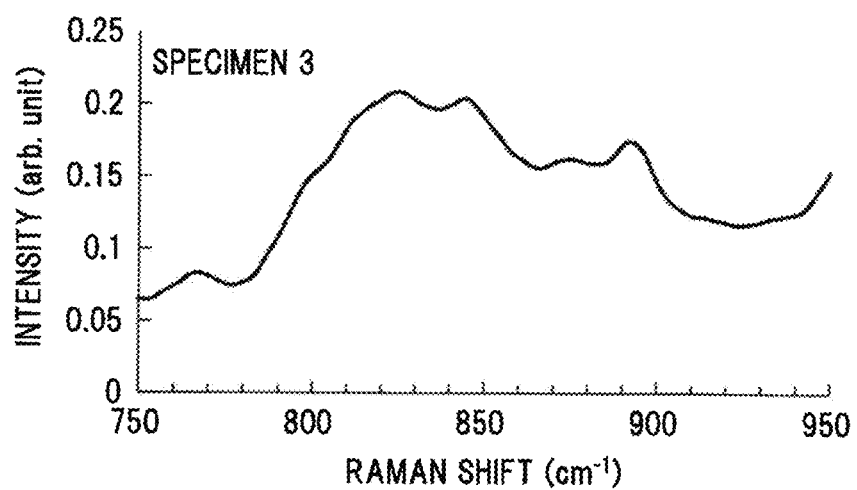
FIG. 6A shows the Raman spectrum for the specimen 3 shown by enlarging a wave number range of from 750 to 950 $cm^{-1}$ in the Raman spectrum for the specimen 3.

FIGS. 4A, 5A, and 6A show the Raman spectra for the specimen 1, the specimen 2, and the specimen 3, respectively, shown by enlarging the wave number ranges of from 750 to 950 cm$^{-1}$ (the ranges surrounded by the broken lines in FIGS. 3A to 3C) in the Raman spectra for the specimen 1, the specimen 2, and the specimen 3, respectively.

intensity ratio" in Table 1 is the value of the ratio of the peak height intensity of the first spectral peak $P_1$ to the peak height intensity of the second spectral peak $P_2$, while the "integral intensity ratio" in Table 1 is the value of the ratio of the integral intensity of the first spectral peak $P_1$ to the integral intensity of the second spectral peak $P_2$.

TABLE 1

| | | Wave number (cm$^{-1}$) | Full width at half maximum (cm$^{-1}$) | Peak height intensity | Peak height intensity ratio | Integral intensity | Integral intensity ratio |
|---|---|---|---|---|---|---|---|
| Specimen 1 | First peak | 893.44 | 12.86 | 967.56 | 0.71 | 13243.3 | 0.33 |
| | Second peak | 846.85 | 27.19 | 1368.79 | | 39614.52 | |
| Specimen 2 | First peak | 892.88 | 11.91 | 732.46 | 0.62 | 9289.38 | 0.26 |
| | Second peak | 849.42 | 28.74 | 1182.88 | | 36183.63 | |
| Specimen 3 | First peak | 893.2 | 11.86 | 596.66 | 0.55 | 7532.62 | 0.23 |
| | Second peak | 846.34 | 23.84 | 1083.18 | | 32218.57 | |

Figure 4B:
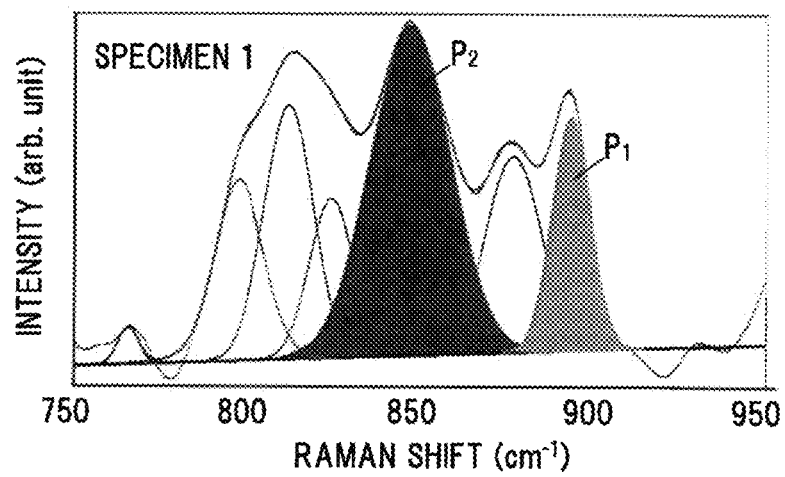
FIG. 4B shows the Raman spectrum for the specimen 1 shown by resolving a plurality of spectral peaks by a spectral deconvolution using the pseudo-Voigt function in a wave number range of from 750 to 950 $cm^{-1}$ in the Raman spectrum for the specimen 1.
Figure 5B:
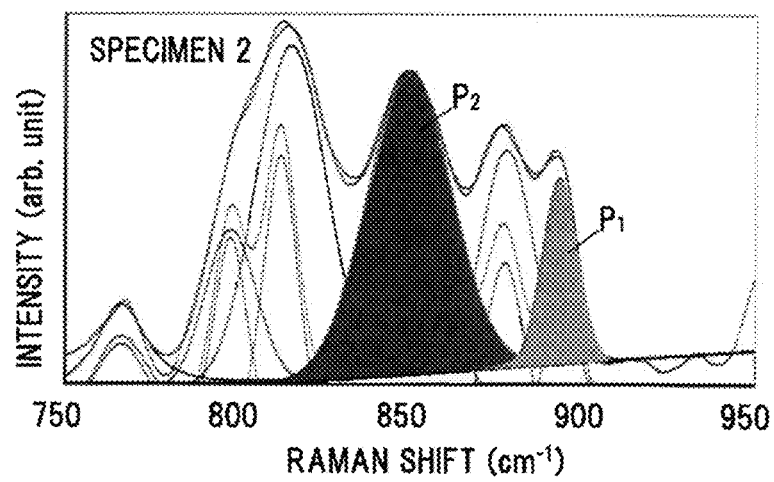
FIG. 5B shows the Raman spectrum for the specimen 2 shown by resolving a plurality of spectral peaks by the spectral deconvolution using the pseudo-Voigt function in a wave number range of from 750 to 950 $cm^{-1}$ in the Raman spectrum for the specimen 2.
Figure 6B:
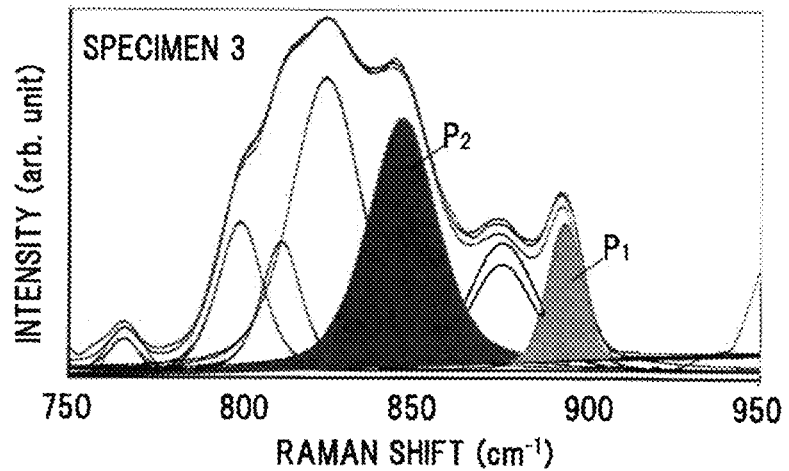
FIG. 6B shows the Raman spectrum for the specimen 3 shown by resolving a plurality of spectral peaks by the spectral deconvolution using the pseudo-Voigt function in a wave number range of from 750 to 950 $cm^{-1}$ in the Raman spectrum for the specimen 3.

FIGS. 4B, 5B, and 6B show the Raman spectra for the specimen 1, the specimen 2, and the specimen 3, respectively, shown by resolving respective pluralities of spectral peaks by a spectral deconvolution (a fitting analysis) using the pseudo-Voigt function in the wave number ranges of from 750 to 950 cm$^{-1}$ in the Raman spectra for the specimen 1, the specimen 2, and the specimen 3, respectively.

Of the plurality of spectral peaks resolved by the spectral deconvolution shown in FIG. 4B, the peak $P_1$ of which the scattering intensity was a maximum value at a wave number of approximately 893 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 847 cm$^{-1}$ was the second spectral peak, which was ascribed to the vibration (the CC symmetric stretching) of the isopropyl groups.

Of the plurality of spectral peaks resolved by the spectral deconvolution shown in FIG. 5B, the peak $P_1$ of which the scattering intensity was a maximum value at a wave number of approximately 893 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 849 cm$^{-1}$ was the second spectral peak, which was ascribed to the vibration (the CC symmetric stretching) of the isopropyl groups.

Of the plurality of spectral peaks resolved by the spectral deconvolution shown in FIG. 6B, the peak $P_1$ of which the scattering intensity was a maximum value at a wave number of approximately 893 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 846 cm$^{-1}$ was the second spectral peak, which was ascribed to the vibration (the CC symmetric stretching) of the isopropyl groups.

Figure 7A:
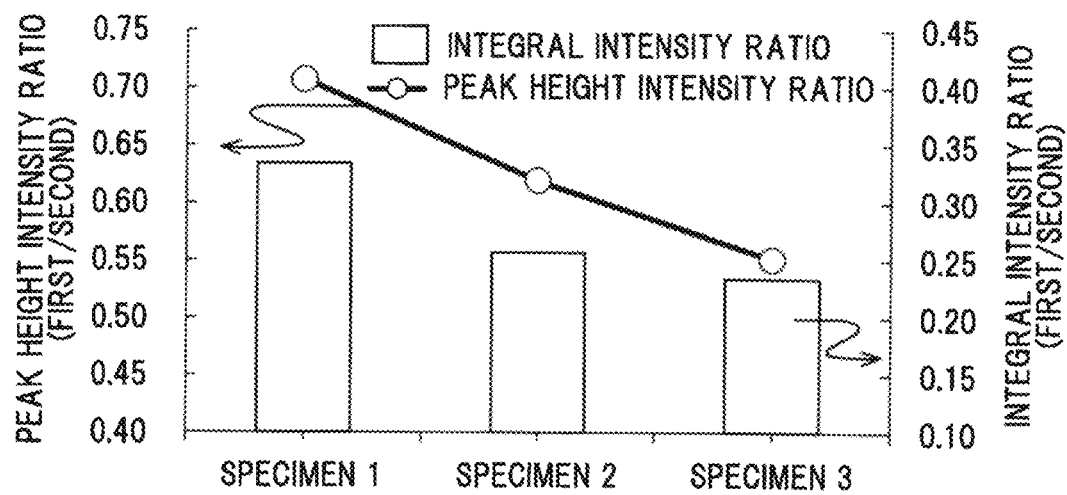
FIG. 7A is a graph showing, for the specimens 1, 2, and 3, respective values of ratios of peak height intensities of respective first spectral peaks to peak height intensities of respective second spectral peaks, and respective values of ratios of integral intensities of the respective first spectral peaks to integral intensities of the respective second spectral peaks, where the first spectral peaks are the peaks ascribed to a vibration of molecular chains in a straight chain hydrocarbon, while the second spectral peaks are the peaks ascribed to a vibration of isopropyl groups.
Figure 7B:
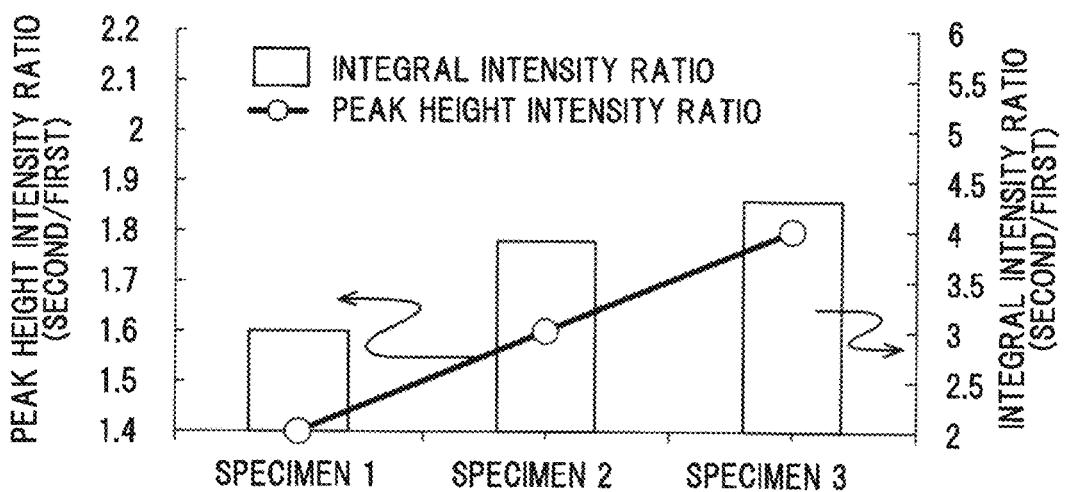
FIG. 7B is a graph showing, for the specimens 1, 2, and 3, respective values of ratios of the peak height intensities of the respective second spectral peaks to the peak height intensities of the respective first spectral peaks, and respective values of ratios of integral intensities of the respective second spectral peaks to integral intensities of the respective first spectral peaks, where the first spectral peaks are the peaks ascribed to the vibration of the molecular chains in the straight chain hydrocarbon, while the second spectral peaks are the peaks ascribed to the vibration of the isopropyl groups.

Table 1 below shows the results of the spectral deconvolution of the Raman spectra for the specimens 1, 2, and 3 in the liquid state (at 26 degrees Celsius). The "peak height FIG. 7A is a graph showing, for the specimens 1, 2, and 3, the respective values of the ratios of the peak height intensities of the respective first spectral peaks to the peak height intensities of the respective second spectral peaks, and the respective values of the ratios of the integral intensities of the respective first spectral peaks to the integral intensities of the respective second spectral peaks. FIG. 7B is a graph showing, for the specimens 1, 2, and 3, the respective values of the ratios of the peak height intensities of the respective second spectral peaks to the peak height intensities of the respective first spectral peaks, and the respective values of the ratios of the integral intensities of the respective second spectral peaks to the integral intensities of the respective first spectral peaks.

Next, the Raman scattering intensity measurement was carried out on the specimens 1, 2, and 3 in a state frozen with a liquid nitrogen. The measurement conditions were rendered unaltered except for the measurement temperatures (the temperatures of the specimens 1, 2, and 3 at the time of the measurement).

FIGS. 8A to 8C show the Raman spectra for the frozen specimens 1, 2, and 3, respectively, measured in a wave number range of from 200 to 1350 cm$^{-1}$. In these Raman spectra of the frozen specimens 1, 2, and 3, the respective spectral peaks at a wave number of approximately 1040 cm$^{-1}$ were the spectral peaks resulting from C—O—C symmetric stretching, while the respective spectral peaks at a wave number of approximately 1280 cm$^{-1}$ were the spectral peaks resulting from vC-O stretching.

Figure 9A:
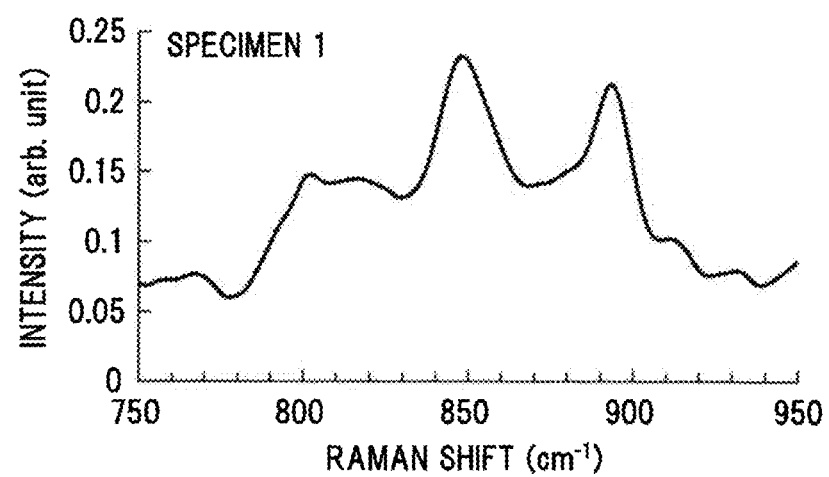
FIG. 9A shows the Raman spectrum for the frozen specimen 1 shown by enlarging a wave number range of from 750 to 950 $cm^{-1}$ in the Raman spectrum for the frozen specimen 1.
Figure 10A:
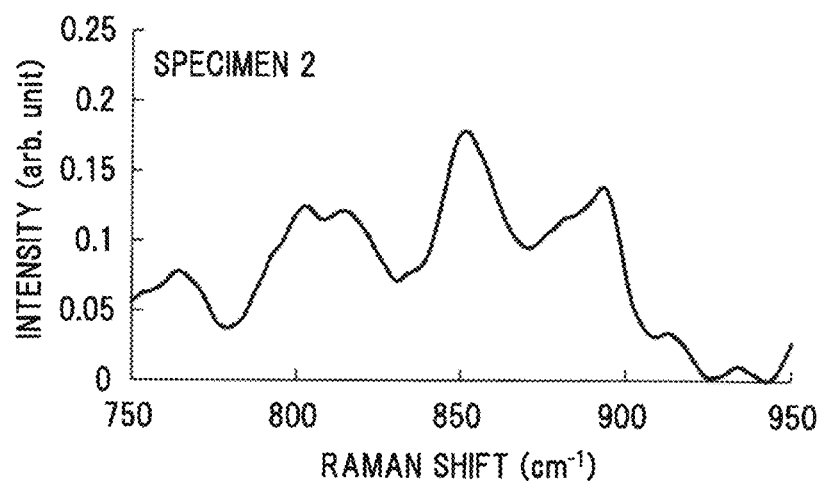
FIG. 10A shows the Raman spectrum for the frozen specimen 2 shown by enlarging a wave number range of from 750 to 950 $cm^{-1}$ in the Raman spectrum for the frozen specimen 2.
Figure 11A:
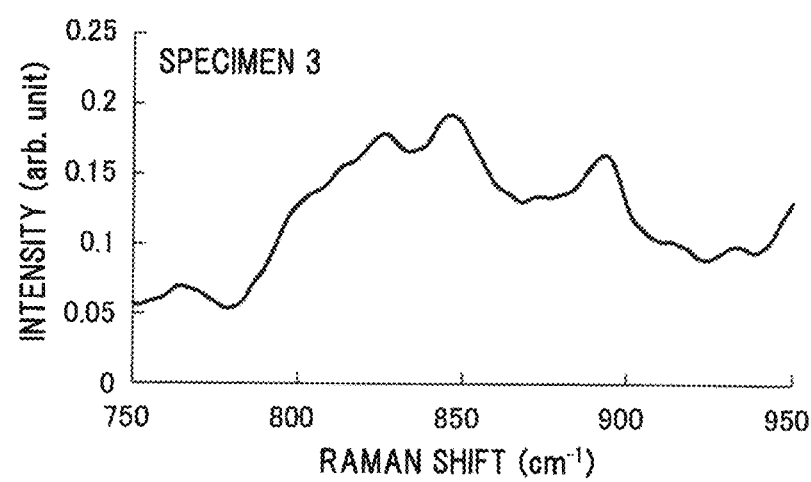
FIG. 11A shows the Raman spectrum for the frozen specimen 3 shown by enlarging a wave number range of from 750 to 950 $cm^{-1}$ in the Raman spectrum for the frozen specimen 3.

FIGS. 9A, 10A, and 11A show the Raman spectra for the frozen specimen 1, the frozen specimen 2, and the frozen specimen 3, respectively, shown by enlarging the wave number ranges of from 750 to 950 cm$^{-1}$ (the ranges surrounded by the broken lines in FIGS. 8A to 8C) in the Raman spectra for the frozen specimen 1, the frozen specimen 2, and the frozen specimen 3, respectively.

Figure 9B:
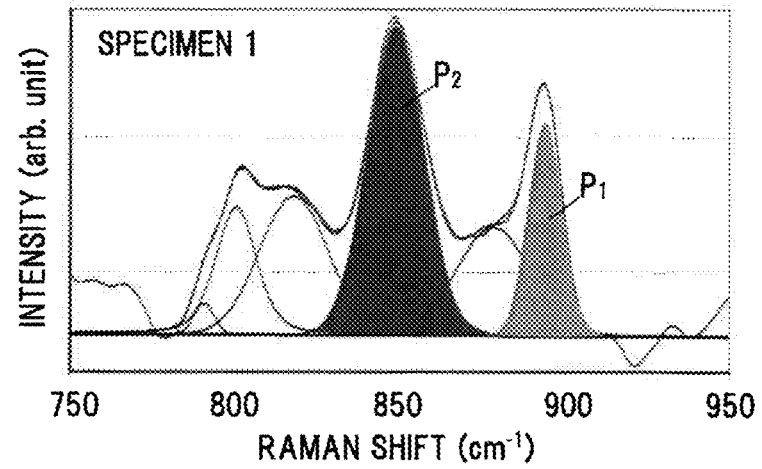
FIG. 9B shows the Raman spectrum for the frozen specimen 1 shown by resolving a plurality of spectral peaks by the spectral deconvolution using the pseudo-Voigt function in a wave number range of from 750 to 950 $cm^{-1}$ in the Raman spectrum for the frozen specimen 1.
Figure 10B:
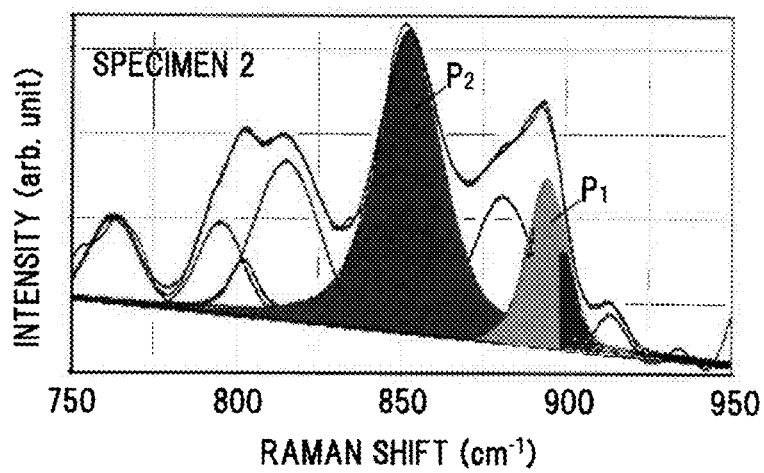
FIG. 10B shows the Raman spectrum for the frozen specimen 2 shown by resolving a plurality of spectral peaks by the spectral deconvolution using the pseudo-Voigt function in a wave number range of from 750 to 950 $cm^{-1}$ in the Raman spectrum for the frozen specimen 2.
Figure 11B:
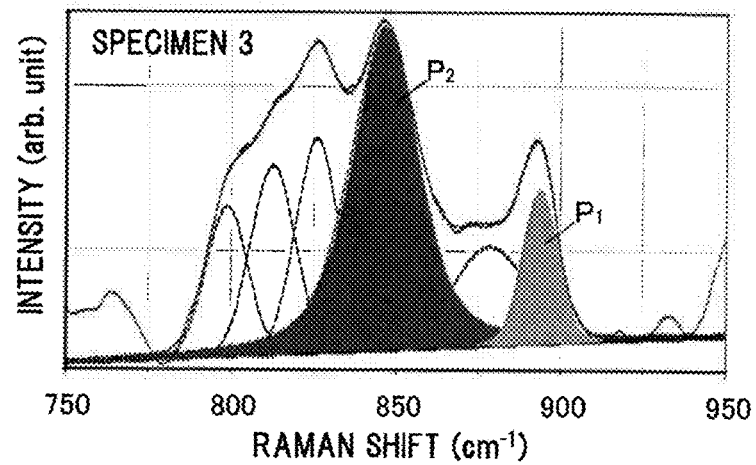
FIG. 11B shows the Raman spectrum for the frozen specimen 3 shown by resolving a plurality of spectral peaks by the spectral deconvolution using the pseudo-Voigt function in a wave number range of from 750 to 950 $cm^{-1}$ in the Raman spectrum for the frozen specimen 3.

FIGS. 9B, 10B, and 11B show the Raman spectra for the frozen specimen 1, the frozen specimen 2, and the frozen specimen 3, respectively, shown by resolving respective pluralities of spectral peaks by a spectral deconvolution (a fitting analysis) using the pseudo-Voigt function in the wave number ranges of from 750 to 950 cm$^{-1}$ in the Raman spectra for the frozen specimen 1, the frozen specimen 2, and the frozen specimen 3, respectively.

Of the plurality of spectral peaks resolved by the spectral deconvolution shown in FIG. 9B, the peak $P_1$ of which the scattering intensity was a maximum value at a wave number of approximately 894 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 849 cm$^{-1}$ was the second spectral peak, which was ascribed to the vibration (the CC symmetric stretching) of the isopropyl groups.

Of the plurality of spectral peaks resolved by the spectral deconvolution shown in FIG. 10B, the peak $P_1$ of which the scattering intensity was a maximum value at a wave number of approximately 894 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 852 cm$^{-1}$ was the second spectral peak, which was ascribed to the vibration (the CC symmetric stretching) of the isopropyl groups.

Of the plurality of spectral peaks resolved by the spectral deconvolution shown in FIG. 11B, the peak $P_1$ of which the scattering intensity was a maximum value at a wave number of approximately 894 cm$^{-1}$ was the first spectral peak, which was ascribed to the vibration (the CC stretching) of the molecular chains in the straight chain hydrocarbon, while the peak $P_2$ of which the scattering intensity was a maximum value at a wave number of approximately 846 cm$^{-1}$ was the second spectral peak, which was ascribed to the vibration (the CC symmetric stretching) of the isopropyl groups.

Table 2 below shows the results of the spectral deconvolution of the Raman spectra for the above described frozen specimens 1, 2, and 3. The "peak height intensity ratio" in Table 2 is the value of the ratio of the peak height intensity of the first spectral peak $P_1$ to the peak height intensity of the second spectral peak $P_2$, while the "integral intensity ratio" in Table 2 is the value of the ratio of the integral intensity of the first spectral peak $P_1$ to the integral intensity of the second spectral peak $P_2$.

FIG. 12A is a graph showing, for the frozen specimens 1, 2, and 3, the respective values of the ratios of the peak height intensities of the respective first spectral peaks to the peak height intensities of the respective second spectral peaks, and the respective values of the ratios of the integral intensities of the respective first spectral peaks to the integral intensities of the respective second spectral peaks. FIG. 12B is a graph showing, for the frozen specimens 1, 2, and 3, the respective values of the ratios of the peak height intensities of the respective second spectral peaks to the peak height intensities of the respective first spectral peaks, and respective values of the ratios of the integral intensities of the respective second spectral peaks to the integral intensities of the respective first spectral peaks.

Figure 13:
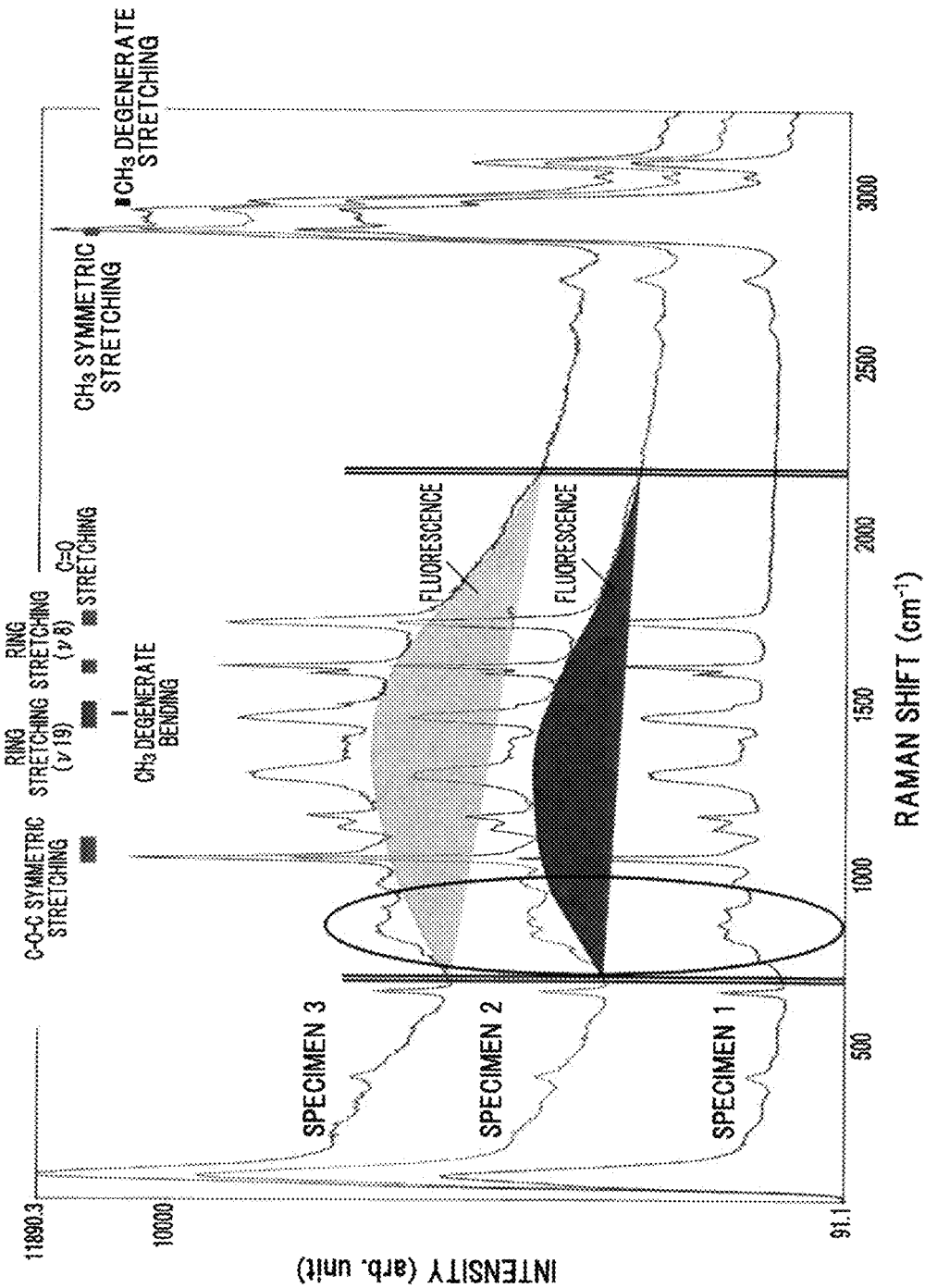
FIG. 13 shows Raman spectra for the specimens 1, 2, and 3 measured in a wave number range of from 0 to 3250 $cm^{-1}$, under a condition of a measurement temperature of 26 degrees Celsius.

FIG. 13 shows Raman spectra for the specimens 1, 2, and 3 measured in a wave number range of from 0 to 3250 cm$^{-1}$ under a condition of a measurement temperature of 26 degrees Celsius. According to FIG. 13, in the Raman spectra for the specimen 2 and the specimen 3, respective broad fluorescence spectra were able to be confirmed over a wave number range of from approximately 700 to approximately 2000 cm$^{-1}$. From these results, it was estimated that the larger the proportion of the branched chain type alkyl chain structures in the DINP, the more unstable the state of the structure of the molecular chain portion of —$C_9H_{19}$, and the larger the number of defect levels generated, therefore resulting in the fluorescence becoming strong. Conversely, it was estimated that the larger the number of straight chain type alkyl chain structures in the DINP, the smaller the proportion of the branched chain type alkyl chain structures in the same DINP, therefore resulting in the fluorescence becoming weak.

Next, the specimens 1 and 3 in the liquid state (at 26 degrees Celsius), and the frozen specimens 1 and 3 were added to the vinyl chloride resins, respectively, and the embrittlement temperatures of the resulting respective vinyl chloride resins were measured.

Table 3 below shows, for the Raman spectra of the specimens 1 and 3 in the liquid state (at 26 degrees Celsius), and of the frozen specimens 1 and 3, the respective values of the ratios (in the column of peak height intensity ratio in Table 3) of the peak height intensities of the respective first spectral peaks to the peak height intensities of the respective second spectral peaks, the respective values of the ratios (in the column of integral intensity ratio in Table 3) of the integral intensities of the respective first spectral peaks to the integral intensities of the respective second spectral peaks, the respective compounding amounts (in the column of compounding ratio in Table 3) per 100 parts by mass of the respective vinyl chloride resins, and the respective embrittlement temperatures (in the column of embrittlement temperature (degrees Celsius) in Table 3) of the resulting respective vinyl chloride resins in which: 50 and 55 parts by

TABLE 2

|  |  | Wave number (cm$^{-1}$) | Full width at half maximum (cm$^{-1}$) | Peak height intensity | Peak height intensity ratio | Integral intensity | Integral intensity ratio |
| --- | --- | --- | --- | --- | --- | --- | --- |
| Specimen 1 | First peak | 893.87 | 11.7 | 162.24 | 0.69 | 2021.11 | 0.40 |
|  | Second peak | 848.67 | 20.32 | 235.62 |  | 5102.82 |  |
| Specimen 2 | First peak | 894.4 | 14.4 | 204.4 | 0.56 | 3489.83 | 0.30 |
|  | Second peak | 852.49 | 23.83 | 367.13 |  | 11581.56 |  |
| Specimen 3 | First peak | 893.55 | 12.15 | 240.2 | 0.47 | 3105.79 | 0.19 |
|  | Second peak | 846.18 | 24.61 | 510.86 |  | 16331.06 |  | mass of the specimens 1 in the liquid state (at 26 degrees Celsius), respectively, were compounded; 50 and 55 parts by mass of the frozen specimens 1, respectively, were compounded; 50 and 55 parts by mass of the specimens 3 in the liquid state (at 26 degrees Celsius), respectively, were compounded; and 50 and 55 parts by mass of the frozen specimens 3, respectively, were compounded.

TABLE 3

| | Peak height intensity ratio | Integral intensity ratio | Compounding ratio | Embrittlement temperature (° C.) |
|---|---|---|---|---|
| Specimen 1 (liquid state) | 0.71 | 0.33 | 50 parts by mass | −25 |
| | | | 55 parts by mass | −29 |
| Specimen 1 (frozen) | 0.69 | 0.40 | 50 parts by mass | −25 |
| | | | 55 parts by mass | −29 |
| Specimen 3 (liquid state) | 0.55 | 0.23 | 50 parts by mass | −24 |
| | | | 55 parts by mass | −28 |
| Specimen 3 (frozen) | 0.47 | 0.19 | 50 parts by mass | −24 |
| | | | 55 parts by mass | −28 |

Figure 14A:
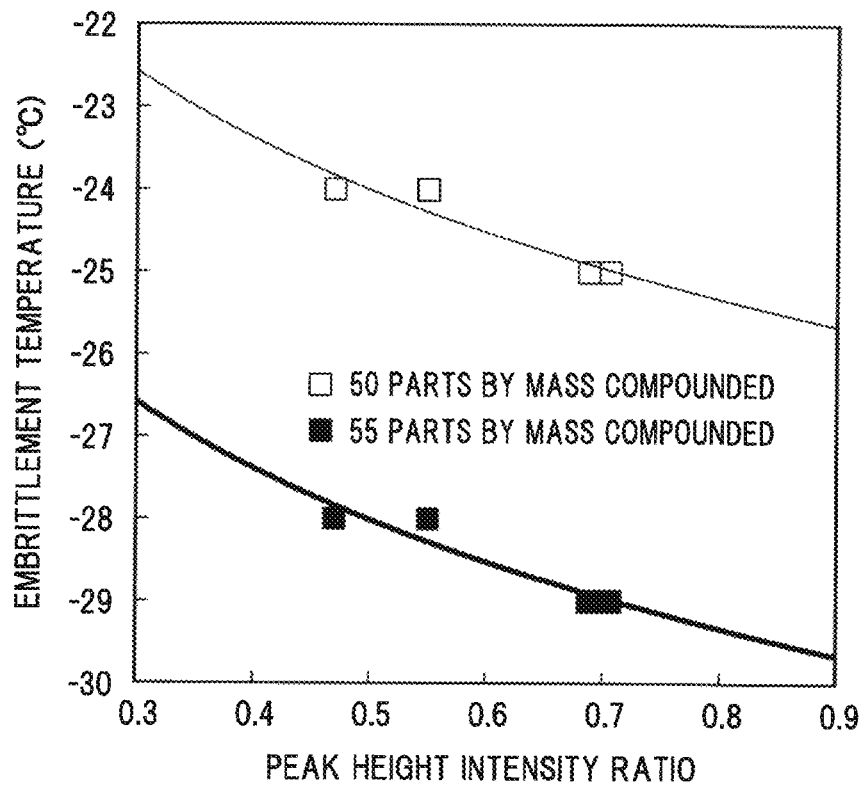
FIG. 14A is a graph showing a respective relationship between the "peak height intensity ratio" and the "embrittlement temperature" for each of the specimens shown in Table 3.
Figure 14B:
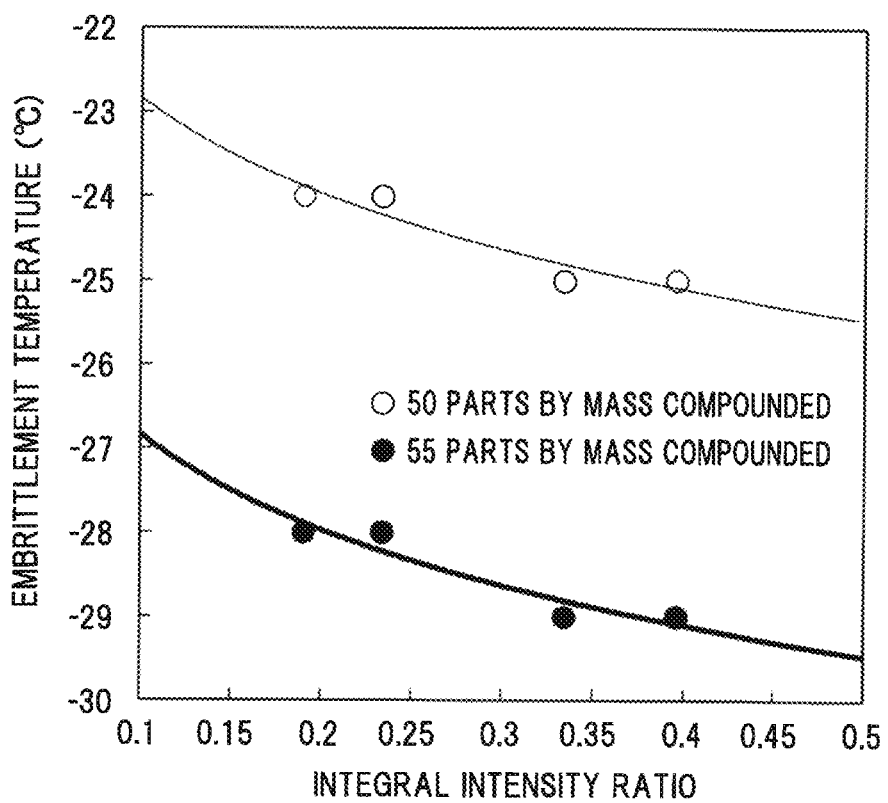
FIG. 14B is a graph showing a respective relationship between the "integral intensity ratio" and the "embrittlement temperature" for each of the specimens shown in Table 3.

FIG. 14A is a graph showing a respective relationship between the "peak height intensity ratio" and the "embrittlement temperature" for each of 50 and 55 parts by mass of the specimens 1 and 3 in the liquid state (at 26 degrees Celsius), and of the frozen specimens 1 and 3 shown in Table 3 above. FIG. 14B is a graph showing a respective relationship between the "integral intensity ratio" and the "embrittlement temperature" for each of 50 and 55 parts by mass of the specimens 1 and 3 in the liquid state (at 26 degrees Celsius), and of the frozen specimens 1 and 3 shown in Table 3.

In Table 3, FIGS. 14A and 14B, it was shown that there were the correlations between the respective intensity ratios of the respective first spectral peaks and the respective second spectral peaks in the respective Raman spectra of the DINPs and the embrittlement temperatures of the resulting respective vinyl chloride resins when the DINPs were compounded into the vinyl chloride resins, respectively. For example, in Table 3 and FIG. 14B, it was shown that the embrittlement temperatures of the resulting respective vinyl chloride resins were able to be effectively reduced by the DINPs, of which the respective values of the ratios of the integral intensities of the respective first spectral peaks to the integral intensities of the respective second spectral peaks measured under the condition of the measurement temperature of 26 degrees Celsius were not less than approximately 0.3, being compounded into the vinyl chloride resins, respectively.

SUMMARY OF THE EMBODIMENT

Next, the technical ideas grasped from the embodiments will be described with the aid of the reference characters and the like in the embodiments. It should be noted, however, that each of the reference characters and the like in the following descriptions is not to be construed as limiting the constituent elements in the appended claims to the members and the like specifically shown in the embodiments.

[1] A quality control method for a diisononyl phthalate, comprising: a measuring step of irradiating the diisononyl phthalate with a laser to measure a Raman spectrum; and an acceptance or rejection decision step of determining an acceptance or a rejection of a quality of the diisononyl phthalate on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum.

[2] The quality control method for the diisononyl phthalate as defined in the above [1], wherein the first spectral peak is a peak of which the intensity is a maximum within a wave number range of not smaller than 880 $cm^{-1}$ and not larger than 900 $cm^{-1}$ in the measured Raman spectrum, while the second spectral peak is a peak of which the intensity is a maximum within a wave number range of not smaller than 840 $cm^{-1}$ and not larger than 860 $cm^{-1}$ in the measured Raman spectrum.

[3] The quality control method for the diisononyl phthalate as defined in the above [1] or [2], wherein, in the acceptance or rejection decision step, when a value of a ratio of an integral intensity of the first spectral peak to an integral intensity of the second spectral peak measured under a condition of a measurement temperature of 26 degrees Celsius is not less than 0.3, a quality of the diisononyl phthalate is regarded as accepted.

[4] The quality control method for the diisononyl phthalate as defined in the above [1] or [2], wherein, in the acceptance or rejection decision step, when a value of a ratio of a peak height intensity of the first spectral peak to a peak height intensity of the second spectral peak measured under a condition of a measurement temperature of 26 degrees Celsius is not less than 0.67, a quality of the diisononyl phthalate is regarded as accepted.

[5] A method for producing a resin composition, comprising a step of adding the diisononyl phthalate regarded as accepted by the quality control method for the diisononyl phthalate as defined in any one of the above [1] to [4] to a polyvinyl chloride.

[6] A resin composition, comprising: a polyvinyl chloride; and a diisononyl phthalate added to that polyvinyl chloride, with the diisononyl phthalate being configured in such a manner that when a Raman spectrum is measured by irradiating the diisononyl phthalate with a laser under a condition of a measurement temperature of 26 degrees Celsius, a value of a ratio of an integral intensity of a first spectral peak, which is ascribed to a vibration of molecular chains in a straight chain hydrocarbon, to an integral intensity of a second spectral peak, which is ascribed to a vibration of isopropyl groups, in the measured Raman spectrum, is not less than 0.3.

[7] A resin composition, comprising: a polyvinyl chloride; and a diisononyl phthalate added to that polyvinyl chloride, with the diisononyl phthalate being configured in such a manner that when a Raman spectrum is measured by irradiating the diisononyl phthalate with a laser under a condition of a measurement temperature of 26 degrees Celsius, a value of a ratio of a peak height intensity of a first spectral peak, which is ascribed to a vibration of molecular chains in a straight chain hydrocarbon, to a peak height intensity of a second spectral peak, which is ascribed to a vibration of isopropyl groups, in the measured Raman spectrum, is not less than 0.67.

[8] The resin composition as defined in the above [6] or [7], wherein the first spectral peak is a peak of which the intensity is a maximum within a wave number range of not smaller than 880 $cm^{-1}$ and not larger than 900 $cm^{-1}$ in the measured Raman spectrum, while the second spectral peak is a peak of which the intensity is a maximum within a wave number range of not smaller than 840 $cm^{-1}$ and not larger than 860 $cm^{-1}$ in the measured Raman spectrum.

[9] A cable (1) or a tube (2), including an electrical insulating member (13, 21) made of the resin composition as defined in any one of the above [6] to [8].

Although the embodiments of the present invention and the examples thereof have been described above, the present invention is not limited to the embodiments and the examples described above, but various modifications can be made without departing from the spirit of the invention. For example, a nuclear magnetic resonance (NMR) intensity measurement may be carried out in place of the Raman scattering intensity measurement, to analyze the spectrum, and thereby investigate the large and small number relationship between the number of branched chain type alkyl chain structures and the number of straight chain type alkyl chain structures in the DINP.

Further, the embodiments and the examples described above are not to be construed as limiting the inventions according to the appended claims. In addition, it should be noted that not all the combinations of the features described in the embodiments are indispensable to the means for solving the problem of the invention.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A quality control method for a plurality of diisononyl phthalates, comprising:
    a measuring step of irradiating each of the plurality of diisononyl phthalates produced under different conditions with a laser to measure a Raman spectrum; and
    an acceptance or rejection decision step of determining an acceptance or a rejection of a quality of each of the plurality of diisononyl phthalates on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum,
    wherein the acceptance or rejection decision step of determining the acceptance or the rejection of the quality is according to a proportion of a straight chain type alkyl chain structures included in each of the plurality of diisononyl phthalates.

2. The quality control method for the plurality of diisononyl phthalates according to claim 1, wherein the first spectral peak is a peak of which the intensity is a maximum within a wave number range of not smaller than 880 $cm^{-1}$ and not larger than 900 $cm^{-1}$ in the measured Raman spectrum, while the second spectral peak is a peak of which the intensity is a maximum within a wave number range of not smaller than 840 $cm^{-1}$ and not larger than 860 $cm^{-1}$ in the measured Raman spectrum.

3. The quality control method for the plurality of diisononyl phthalates according to claim 1, wherein, in the acceptance or rejection decision step, when a value of a ratio of an integral intensity of the first spectral peak to an integral intensity of the second spectral peak measured under a condition of a measurement temperature of 26 degrees Celsius is not less than 0.3, a quality of each of the plurality of diisononyl phthalates is regarded as accepted.

4. The quality control method for the plurality of diisononyl phthalates according to claim 1, wherein, in the acceptance or rejection decision step, when a value of a ratio of a peak height intensity of the first spectral peak to a peak height intensity of the second spectral peak measured under a condition of a measurement temperature of 26 degrees Celsius is not less than 0.67, a quality of each of the plurality of diisononyl phthalates is regarded as accepted.

5. A method for producing a resin composition, comprising:
    a step of adding the plurality of diisononyl phthalates regarded as accepted by the quality control method for the plurality of diisononyl phthalates according to claim 1 to a polyvinyl chloride.

6. A quality control method for a plurality of diisononyl phthalates, comprising:
    a measuring step of irradiating each of the plurality of diisononyl phthalates produced under different conditions with a laser to measure a Raman spectrum; and
    an acceptance or rejection decision step of determining an acceptance or a rejection of a quality of each of the plurality of diisononyl phthalates on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum,
    wherein the determining the acceptance or the rejection of the quality of each of the plurality of diisononyl phthalates is on the basis of a ratio of the first spectral peak and the second spectral peak.

7. The quality control method for the plurality of diisononyl phthalates according to claim 6, wherein the first spectral peak is a peak of which the intensity is a maximum within a wave number range of not smaller than 880 $cm^{-1}$ and not larger than 900 $cm^{-1}$ in the measured Raman spectrum, while the second spectral peak is a peak of which the intensity is a maximum within a wave number range of not smaller than 840 $cm^{-1}$ and not larger than 860 $cm^{-1}$ in the measured Raman spectrum.

8. The quality control method for the plurality of diisononyl phthalates according to claim 6, wherein, in the acceptance or rejection decision step, when a value of a ratio of an integral intensity of the first spectral peak to an integral intensity of the second spectral peak measured under a condition of a measurement temperature of 26 degrees Celsius is not less than 0.3, a quality of each of the plurality of diisononyl phthalates is regarded as accepted.

9. The quality control method for the plurality of diisononyl phthalates according to claim 6, wherein, in the acceptance or rejection decision step, when a value of a ratio of a peak height intensity of the first spectral peak to a peak height intensity of the second spectral peak measured under a condition of a measurement temperature of 26 degrees Celsius is not less than 0.67, a quality of each of the plurality of diisononyl phthalates is regarded as accepted.

10. A method for producing a resin composition, comprising:
    a step of adding the plurality of diisononyl phthalates regarded as accepted by the quality control method for the plurality of diisononyl phthalates according to claim 6 to a polyvinyl chloride.

11. A quality control method for a plurality of diisononyl phthalates, comprising:
    a measuring step of irradiating each of the plurality of diisononyl phthalates produced under different conditions with a laser to measure a Raman spectrum; and
    an acceptance or rejection decision step of determining an acceptance or a rejection of a quality of each of the plurality of diisononyl phthalates on the basis of a high and low intensity relationship between an intensity of a first spectral peak, which is ascribed to a vibration of molecular chains in a straight chain hydrocarbon, and an intensity of a second spectral peak, which is ascribed to a vibration of isopropyl groups, in the measured Raman spectrum, wherein each of the plurality of diisononyl phthalates includes a straight chain type alkyl chain structure that is used to measure the first spectral peak and the second spectral peak.

12. The quality control method for the plurality of diisononyl phthalates according to claim 11, wherein the first spectral peak is a peak of which the intensity is a maximum within a wave number range of not smaller than 880 $cm^{-1}$ and not larger than 900 $cm^{-1}$ in the measured Raman spectrum, while the second spectral peak is a peak of which the intensity is a maximum within a wave number range of not smaller than 840 $cm^{-1}$ and not larger than 860 $cm^{-1}$ in the measured Raman spectrum.

13. The quality control method for the plurality of diisononyl phthalates according to claim 11, wherein, in the acceptance or rejection decision step, when a value of a ratio of an integral intensity of the first spectral peak to an integral intensity of the second spectral peak measured under a condition of a measurement temperature of 26 degrees Celsius is not less than 0.3, a quality of each of the plurality of diisononyl phthalates is regarded as accepted.

14. The quality control method for the plurality of diisononyl phthalates according to claim 11, wherein, in the acceptance or rejection decision step, when a value of a ratio of a peak height intensity of the first spectral peak to a peak height intensity of the second spectral peak measured under a condition of a measurement temperature of 26 degrees Celsius is not less than 0.67, a quality of each of the plurality of diisononyl phthalates is regarded as accepted.

15. A method for producing a resin composition, comprising:

a step of adding the plurality of diisononyl phthalates regarded as accepted by the quality control method for the plurality of diisononyl phthalates according to claim 11 to a polyvinyl chloride.

* * * * *